United States Patent
Garito et al.

(10) Patent No.: US 6,749,608 B2
(45) Date of Patent: Jun. 15, 2004

(54) ADENOID CURETTE ELECTROSURGICAL PROBE

(76) Inventors: Jon C. Garito, 1135 Railroad Ave., Hewlett, NY (US) 11557; Alan G. Ellman, 1135 Railroad Ave., Hewlett, NY (US) 11557

( * ) Notice: Subject to any disclaimer, the term of this patent is extended or adjusted under 35 U.S.C. 154(b) by 99 days.

(21) Appl. No.: 10/211,385

(22) Filed: Aug. 5, 2002

(65) Prior Publication Data

US 2004/0024401 A1 Feb. 5, 2004

(51) Int. Cl.$^7$ .............................................. A61B 18/18
(52) U.S. Cl. ........................................... 606/45; 606/41
(58) Field of Search ............................ 606/41, 45–50; 604/35

(56) References Cited

U.S. PATENT DOCUMENTS

| | | | |
|---|---|---|---|
| 1,881,250 A | | 10/1932 | Milton |
| 4,221,222 A | | 9/1980 | Detsch |
| 5,324,288 A | * | 6/1994 | Billings et al. ............... 606/45 |
| 5,423,812 A | * | 6/1995 | Ellman et al. ................ 606/45 |
| 5,505,728 A | * | 4/1996 | Ellman et al. ................ 606/39 |
| 5,683,387 A | * | 11/1997 | Garito et al. ................ 606/45 |
| 5,746,746 A | * | 5/1998 | Garito et al. ................ 606/41 |
| 6,080,152 A | | 6/2000 | Nardella et al. |
| 6,348,051 B1 | * | 2/2002 | Farin et al. ................... 606/49 |
| 6,530,924 B1 | * | 3/2003 | Ellman et al. ................ 606/45 |
| 6,562,036 B1 | * | 5/2003 | Ellman et al. ................ 606/45 |

FOREIGN PATENT DOCUMENTS

| | | |
|---|---|---|
| DE | 91 02 778 U | 5/1991 |
| DE | 198 50 663 A | 3/2001 |
| DE | 201 10 351 A | 2/2002 |

* cited by examiner

*Primary Examiner*—Michael Peffley

(57) ABSTRACT

An electrosurgical curette probe for an adenoidectomy procedure, comprising an elongated electrically-insulating body portion having at a proximate end an electrical connector for receiving electrosurgical RF currents and a fitting for receiving a suction conduit. The electrical connector is internally connected to an active electrode at the distal end of the body portion, which active electrode comprises a bare sharp blade extending across the spaced arms of a claw-shaped end of the body portion. Viewed from the top, the claw-shaped end curves downward, the blade extends in a direction perpendicular to an extension of the longitudinal axis of the body portion, and the sharp cutting edge of the blade faces upwardly. Terminating just behind the claw-shaped end and facing the curved claw-shaped end is a nozzle opening of the suction conduit housed in the body portion and connected to the fitting.

9 Claims, 2 Drawing Sheets

ADENOID CURETTE ELECTROSURGICAL PROBE

This invention relates to an electrosurgical electrode for an adenoidectomy surgical procedure.

BACKGROUND OF THE INVENTION

Adenoidectomy is indicated for the relief of nasal obstruction, sleep apnea, recurrence of chronic infection, and for chronic ear disease. The procedure is the surgical removal of hypertrophic adenoid tissue from the posterior nasal cavity and along the torus. The procedure as such is well known using conventional curettes and is described in detail in Surgical Pediatric Otolaryngology edited by Potsic, Cotton, and Handler, Pages 234–235 and FIG. 20-1A–H, published 1997 by Thieme of New York, the contents of which are incorporated herein by reference.

Adenoidectomy continues to be one of the most commonly performed operations in children in the 20th Century. The gold standard for adenoidectomy is the conventional curette. A major problem using conventional curettes besides persistent bleeding is visualization. Moreover, general anesthesia is always required and a 1–3 day hospitalization of the patient as well. Postoperative packing of the surgerized area is always needed to control and contain post-operative bleeding. A special liquid diet is always prescribed post-operatively.

SUMMARY OF THE INVENTION

An object of the invention is an improved adenoidectomy surgical procedure.

We have invented a novel unipolar electrode for use in an electrosurgical adenoidectomy procedure. This electrosurgical procedure using our novel electrode enables physicians to offer to patients a treatment that is efficiently performed, easily learned and thus performed at a significantly reduced price, and with less tissue damage and superior results compared to procedures done with a scalpel-curette.

The procedure using our novel electrode is based on the incising of a portion or all of an area of the adenoid by intranasal electrosurgery, i.e., via the nasal passageway. The electrode of the invention is uniquely configured to enable the active tip to reach and incise the hypertrophic adenoid tissue while avoiding damage to surrounding tissue.

In a preferred embodiment, our novel electrode is characterized by an elongated electrically-insulating body portion having at a proximate end an electrical connector for receiving electrosurgical RF currents and a fitting for receiving a suction conduit. The electrical connector is internally connected to an active electrode at the distal end of the body portion, which active electrode comprises a bare sharp blade extending across the arms of a claw-shaped end of the body portion. Viewed from the top, the claw-shaped end curves downward, the blade extends in a direction perpendicular to an extension of the longitudinal axis of the body portion, and the sharp cutting edge of the blade faces upwardly. Terminating just behind the claw-shaped end and facing the curved claw-shaped end is a nozzle opening of a suction conduit housed in the body portion and connected to the fitting. The tissue excising is effected with the bare blade cutting edge moved by the surgeon in a generally upward path after the elongated body portion has been introduced into the nasal cavity. The insulated parts of the body portion help position and guide the active blade edge during the surgical procedure. The electrosurgical procedure has the very important advantage of being able to excise the adenoid tissue portions while at the same time coagulating the cut tissue causing minimum bleeding. It is preferred that the electrosurgical currents used be above 2 MHz, and preferably above 3 MHz. At these RF high frequencies, commonly referred to as radiosurgery, cutting is accomplished by volatilizing intracellular fluids at the point of the transmitting electrode contact which is primarily responsible for only small lateral heat spread and thus less damage to neighboring cell layers by keeping tissue temperature lower.

The advantages of using the RF adenoid curette of the invention include:

a) the procedure can be done in the office and a hospital environment is unnecessary as the RF adenoid curette procedure is done with local anesthesia not general;

b) the RF low temperature energy source connected to the RF adenoid curette probe enables precise micro cutting of the curette RF blade into adenoid tissue;

c) no post-operative packing is normally necessary;

d) there is a clear unobstructed view of the surgical site with the adenoid probe of the invention;

e) no special diet is necessary.

When used herein with respect to the probe of the invention, the term "downward" means, with the probe held horizontally with its longitudinal axis extending horizontally, as illustrated in FIG. 1 below, in a southerly direction (toward the bottom margin of the drawing) transverse to the longitudinal axis. The term "below" means positioned underneath the axis with the probe held in the same position shown in the drawing. The term "upward" means in the reverse northerly direction, and the term "above" similarly means above the axis with the probe held in the same position shown in the drawing.

DETAILED DESCRIPTION OF THE PREFERRED EMBODIMENTS

The novel design of the invention not only provides a sharp blade edge positioned for precise micro-cutting to remove well-defined segments of tissue exactly where the RF probe is placed, but in addition the suction provided just inside the claw simultaneously evacuates blood, tissue and RF plume from the surgical field for a clearer view. Adenoid tissue at the superior choana and along the torus tubarius can be shaved and sculpted away very easily. The increased surgical accuracy allows easy removal of hypertrophic adenoid tissue from the posterior nasal cavity and along the torus. Thus, a more thorough and complete adenoidectomy is readily accomplished. Due to the use of RF megahertz frequencies, lower temperatures are maintained, tissue regrowth and symptom reference are minimized, and post-operative pain tends to be reduced.

Figure 1:
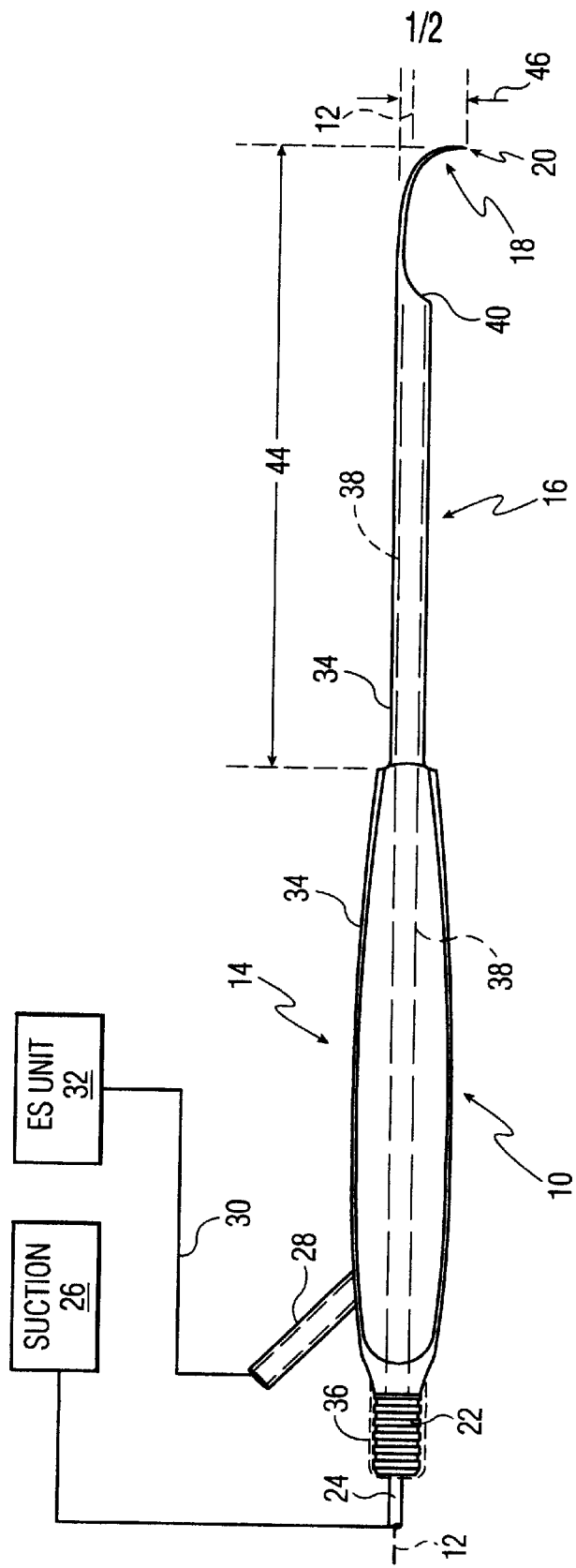
FIG. 1 is a side view of one form of adenoid probe of the invention shown connected to electrosurgical apparatus and a suction generator.

FIG. 1 illustrates a preferred form of the novel electrosurgical probe 10 of the invention. It comprises an elongated structure having a central axis 12 including at a proximate first end (at the left of FIG. 1) a handle 14 and at the opposite distal second end a shaft 16 terminating in a downwardly extending claw 18 from the bottom of which is suspended a cutting blade 20 (not visible as such in FIG. 1). At the first end is mounted a fitting 22 for receiving a conduit (shown schematically) 24 capable of supporting suction. The conduit in turn is connected to a conventional suction generator 26. At the same first end is mounted a female electrical connector 28 which is connected via a cable 30 in the conventional manner to conventional electrosurgical apparatus 32. As an example only, and not meant to be limiting, the electrosurgical apparatus 32 can be model AAOP Surgitron FFPF or the Dual-Frequency Unit available from the Ellman company of Hewlett, N.Y. The Ellman equipment is preferred due to its high operating frequency, typically over 2 MHz, preferably at 3.8 MHz.

The handle 14 and shaft 16 as a unitary body are constructed of electrically-conductive material, such as stainless steel, but the entire assembly, except for the fitting 22 and the blade 20 are completely covered with an insulating coating 34 such that the only electrically exposed parts are the fitting 22 and the blade 20. The electrical connector 28 is electrically connected to the electrically-conductive body. The result is that the metallic blade 20, for example, of stainless steel, mounted on the claw end 18, is electrically connected to the electrically-conductive body and thus to the electrical connector 28. Hence, when the electrosurgical unit 32 is activated, electrosurgical currents flow via the connector 28 to the body and in turn to the cutting blade 20. The fitting 20 in use is typically covered by the plastic cable end 36. Hence, during use, the entire assembly is shielded from the electrosurgical currents except for the cutting blade 20 which serves as the active electrode.

Extending longitudinally through the body is a tube 38, for example of stainless steel. The proximate end of the tube 38 is pneumatically coupled to the suction fitting 22, and at the distal end terminates in an opening 40 that faces the inside of the claw 18, below the axis 12. Suction generated by the generator 26 is conducted via the fitting 22 and the internal tube 38 to the opening 40 when the suction generator is activated.

Figure 2:
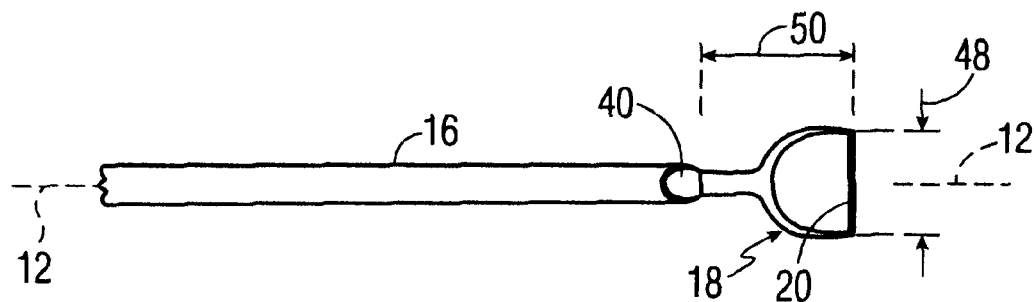
FIG. 2 is a bottom view of the electrode portion of FIG. 1.
Figure 3:
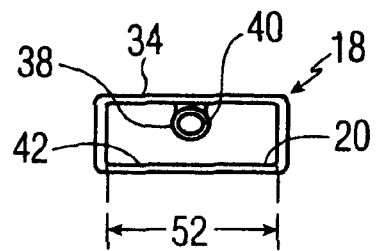
FIG. 3 is a front view of the probe of FIG. 1 from the right side of FIG. 1.

In order for the probe to perform an adenoidectomy, certain dimensions are critical, as the probe in order to reach the adenoid tissue is introduced via a nasal passage and must be able to navigate that passage such that the blade is located under the tissue to be excised. In the preferred embodiment, the upper edge designated 42 is sharpened, so that a cutting action occurs when the blade with its sharpened cutting edge 42 contacting or nearly contacting the tissue is swept upwardly while the electrosurgical unit is activated. The important dimensions are the length of the shaft 16 including the claw 18, designated in FIG. 1 as 44. Also important are the height 46 of the claw which includes the blade 20; the width 48 (FIG. 2) of the claw part that supports the blade 20; and the axial spacing 50 between the suction opening 40 and the cutting blade 20. The latter is important as it determines the efficiency of the suction effect at the surgical site. The horizontal dimension indicated at 52 in FIG. 3 designates the bare active part of the blade. The blade preferably is narrow, with a height of about 1–2 mm. The blade corners are also covered by the electrically-insulating coating 34. The claw 18 extends downwardly essentially transverse to the longitudinal axis 12. The blade 20 thus extends also essentially transversely to the longitudinal axis but perpendicular to the claw ends (into the plane of the drawing of FIG. 1). The preferred dimensions for these parts are as follows:

a) length 44 of the shaft 16 including the claw 18—10.0–11.5, preferably, 10.8, cm;
  b) height 46 of the claw which includes the blade 20—12.0–13.0, preferably, 12.5, mm;
  c) width 48 of the claw part that supports the blade 20—12.0–13.0, preferably, 12.5, mm;
  d) axial spacing 50 between the suction opening 40 and the cutting blade 20—19.0–20.0, preferably, 19.5, mm.

The entire structure which constitutes a unipolar probe is stiff and sturdy and does not flex during use. The dimensions may be reduced for use of the probe with very small children. Also connected to the electrosurgical unit 32 is the usual indifferent plate which during use is in contact with the patient's body. When the electrosurgical apparatus 32 and suction generator 26 are energized, high frequency electrosurgical currents are generated which are coupled by way of the electrically conductive tube 38 of the probe to the active blade end 20. The physician, in the usual way, holds the handle 14 while applying the working end 20 of the probe to the desired area of the patient to be treated.

The electrically insulating coating 34 may be of plastic, Teflon being one example. The use of the probe will be better understood from the following example.

After the patient has been pre-medicated with an appropriate oral analgesia and placed on his back with his head back, and under local anesthesia, the surgeon introduces the instrument through the nasal cavity with the claw-shaped end 18 facing downward and then into the nasopharynx until the cutting edge 42 is positioned below the adenoid tissue to be excised—shaved or sculpted. After activating the electrosurgical apparatus and activating the suction source, using a suitable fulcrum, the cutting end 42 is slowly moved upward. The shaved or excised tissue, any smoke or blood, is evacuated under the suction produced at the suction nozzle end 40 which is closely spaced to and thus effective at the claw interior and thus at the surgical site. The electrosurgical currents simultaneously with the excising will coagulate any bleeders avoiding the necessity for nasal packing. The procedure can be repeated to remove any residual adenoid tissue from the posterior nasal cavity and along the torus.

The procedure has some similarity to that described in our U.S. Pat. No. 5,571,101 for an area of the nasal mucosa, except that the electrode shaft of the electrode of the invention is considerably longer, 3–4 times longer, in order to reach down to the adenoid tissue, and instead of an L-shaped needle, an inversed transverse cutting edge 42 is employed suspended from the lower edge of the downwardly-projected claw-shaped end 18 terminating the shaft. With the Ellman equipment, the fully rectified or cut/coag current is used at a power setting of about 3–4. There is very little trauma and the "sore throat" felt by the patient is easily handled by analgesia and anti-inflammatory drugs.

From the description and drawings it will be clear that the electrically insulating coating 34 on all but the bare cutter 20 functions to prevent undesired contact and possible burns by those members to adjoining and surrounding tissue.

The procedure described can be effective in reducing the effects of adenoid tissue disorders, and offers the advantages of avoiding the mechanical scalpels or curettes, bleeding, and much patient trauma, pre-surgery and post-surgery.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical probe for excising of adenoid tissue, comprising:
   (a) an elongated body portion having a longitudinal axis and comprising at a proximate end an electrical connector for receiving electrosurgical RF currents and a fitting for receiving suction,
   (b) a suction conduit within the body portion and connected at one end to the fitting,
   (c) the body portion having at a distal end a claw-shaped member comprising spaced arms, viewed from the top, the claw-shaped member curves downward,
   (d) an active electrode at the distal end of the body portion, the active electrode comprising a bare sharp blade extending across the arms of the claw-shaped member,
   (e) means for connecting the electrical connector to the bare sharp blade,
   (f) the suction conduit having at the distal end an opening facing the interior of the claw-shaped member,
   (g) portions of said body portion except for the bare sharp blade being electrically insulating to prevent contact and passage of electrosurgical currents to areas adjacent to or surrounding the tissue to be excised when electrosurgical currents are supplied to the electrical connector and suction applied to the fitting during an adenoidectomy,
   (h) the blade having a sharp cutting edge and the sharp cutting edge facing upwardly toward the interior of the claw-shaped member.

2. An electrosurgical probe as claimed in claim 1, wherein the blade extends in a direction perpendicular to an extension of the longitudinal axis of the body portion.

3. An electrosurgical probe as claimed in claim 2, wherein the body portion is stiff and electrically-conductive but is coated with an electrically insulating coating.

4. An electrosurgical probe as claimed in claim 1, wherein the body portion comprises a handle part and a shaft connected to the claw-shaped member, the length of the shaft including the claw-shaped member is about 10.0–11.5 cm.

5. An electrosurgical probe as claimed in claim 1, wherein the height of the claw-shaped member including the blade is about 12.0–13.0 mm.

6. An electrosurgical probe as claimed in claim 5, wherein the width of the claw-shaped member is about 12.0–13.0 mm.

7. An electrosurgical probe as claimed in claim 4, wherein the axial spacing between the suction opening and the cutting blade is about 19.0–20.0 mm.

8. In combination:
   (1) electrosurgical apparatus capable of supplying high frequency electrosurgical currents,
   (2) a suction generator,
   (3) an electrosurgical probe for excising of adenoid tissue, comprising:
      (a) an elongated body portion having a longitudinal axis and comprising at a proximate end an electrical connector connected to the electrosurgical apparatus for receiving electrosurgical RF currents and a fitting connected to the suction generator for receiving suction,
      (b) a suction conduit within the body portion and connected at one end to the fitting,
      (c) the body portion having at a distal end a claw-shaped member comprising spaced arms, viewed from the top, the claw-shaped member curves downward,
      (d) an active electrode at the distal end of the body portion, the active electrode comprising a bare sharp blade extending across the arms of the claw-shaped member, the blade having a sharp cutting edge and the sharp cutting edge facing upwardly toward the interior of the claw-shaped member,
      (e) means for connecting the electrical connector to the bare sharp blade,
      (f) the suction conduit having at the distal end an opening facing the interior of the claw-shaped member,
      (g) portions of said body portion except for the bare sharp blade being electrically insulating to prevent contact and passage of electrosurgical currents to areas adjacent to or surrounding the tissue to be excised when the electrosurgical apparatus and suction generator are activated and electrosurgical currents supplied to the electrical connector and suction applied to the fitting during an adenoidectomy.

9. The combination of claim 8, wherein the high frequency currents are at a frequency exceeding 2 MHz.

* * * * *